United States Patent [19]

Gui et al.

[11] Patent Number: 5,744,674
[45] Date of Patent: Apr. 28, 1998

[54] CATALYST AND PROCESS FOR THE CONVERSION OF HEAVY AROMATICS TO LIGHT AROMATICS

[75] Inventors: Shouxi Gui; Yuzhi Hao; Yanqing Li; Zhenhua Jing; Haohui Gu; Zhanqiao Liang; Baoyu Cheng, all of Beijing, China

[73] Assignees: China Petrochemical Corporation; Research Institute of Petroleum Processing, both of Beijing, China

[21] Appl. No.: 597,157

[22] Filed: Feb. 6, 1996

[51] Int. Cl.[6] ........................................ C07C 4/12
[52] U.S. Cl. .................... 585/489; 502/64; 502/65; 502/66; 502/71; 502/70; 502/77; 502/81; 502/84; 502/325; 502/339; 502/332; 502/349; 502/351; 585/488; 585/486
[58] Field of Search ................ 502/64, 65, 66, 502/71, 70, 77, 81, 84, 325, 339, 332, 349, 351; 585/489, 488, 486

[56] References Cited

U.S. PATENT DOCUMENTS

| | | | |
|---|---|---|---|
| 4,341,622 | 7/1982 | Tabak et al. | 208/66 |
| 4,738,941 | 4/1988 | Dufresne et al. | 502/66 |
| 4,933,487 | 6/1990 | Hoelderich et al. | 560/205 |
| 5,001,296 | 3/1991 | Howley et al. | 585/489 |
| 5,043,513 | 8/1991 | Howley et al. | 585/489 |
| 5,271,920 | 12/1993 | Chang et al. | 423/700 |

FOREIGN PATENT DOCUMENTS 85 1 00218 B  11/1987  China.

*Primary Examiner*—Walter D. Griffin
*Assistant Examiner*—Nadine Preisch
*Attorney, Agent, or Firm*—Burns, Doane, Swecker & Mathis LLP

[57] ABSTRACT

A catalyst for the preparation of benzene, toluene and xylene from $C_9^+$ heavy aromatics consists of zeolite ZSM-5 and $\gamma$- or $\eta$-$Al_2O_3$ as carrier, Re, Sn and Pt or Pd supported on the carrier. Under the conditions of 350°–450° C., 0.5–3.5 MPa, a WHSV of 1–5 $h^{-1}$ and a $H_2$/HC ratio (v/v) of 500–1200, the catalyst achieves high activity and stability as well as low hydrogen consumption.

12 Claims, No Drawings

CATALYST AND PROCESS FOR THE CONVERSION OF HEAVY AROMATICS TO LIGHT AROMATICS

FIELD OF THE INVENTION

The present invention relates to a catalyst for the conversion of heavy aromatics to light aromatics, a method for preparing said catalyst and a process for the same conversion therewith. More particularly, this invention relates to a catalyst containing a synthetic aluminosilicate zeolite and noble metals for the conversion of $C_9^+$ heavy aromatics to light aromatics to produce benzene, toluene and xylene (hereafter refered to as BTX), a method for preparing said catalyst and a process for the same conversion therewith.

BACKGROUND OF THE INVENTION

Heavy aromatics are present mainly in the products obtained by catalytic reforming and in the cracking gasoline obtained during the cracking process of hydrocarbons for the preparation of ethylene. Generally speaking, these heavy aromatics have been used substantially as fuels except that a very small part of them has been used as solvents, and it is anticipated that in the near future the output of heavy aromatics will increase, therefore, how to utilize heavy aromatics comprehensively and effectively is an important task waited to be solved.

U.S. Pat. No. 4,341,622 discloses a process for converting ethylbenzene and alkylbenzenes of more than eight carbon atoms to BTX, wherein side chains of two or more carbon atoms are removed from the benzene rings in the presence of the catalyst of low acidity and activity containing zeolite and a metal possessing hydrogenation/dehydrogenation activity under the reaction conditions of 800°–1000° F. (427°–540° C.), 200 psig and a liquid hourly space velocity of 5 $h^{-1}$, thus converting ethylbenzene to benzene, methylethylbenzene to toluene, dimethyl-ethylbenzene to xylene and the like. The zeolite used in the catalyst is a crystalline aluminosilicate zeolite having a constraint index of 1 to 12, a pore size of more than 5 Å, a silica/alumina ratio of at least 12, more preferably greater than 200, most preferably greater than 500, such as zeolite ZSM-5, ZSM-11, ZSM-12, ZSM-35, ZSM-38 and the like. The metal components possessing hydrogenation/dehydrogenation activity used in the catalyst are selected from the metals of Group VIII of the Periodic Table of Elements, preferably a noble metal such as Pt or Pd. For example, when the industrial reformate above 305° F. containing 89.4% by weight of $C_9^+$ aromatics are used as feedstock, contact of the $C_9^+$ heavy aromatics with a catalyst comprising 65% by weight of zeolite ZSM-5 of a silica/alumina ratio of 1600, 35% by weight of $Al_2O_3$ and 0.1% by weight of Pt under the conditions of 900° F. (480° C.), 200 psig, a weight hourly space velocity of 10 $h^{-1}$ and a hydrogen/hydrocarbon ratio (by mole) of 5 will give a net yield of benzene, toluene and xylene of 3.62–4.25% by weight, 14.92–17.42% by weight and 6.47–7.64% by weight respectively, based on the total weight of the feedstock. The selectivity calculated by dividing the net yield of $C_8^-$ aromatics by the conversion of the $C_9^+$ feedstock is 70–73%.

U.S. Pat. No. 5,001,296 discloses a process for the hydrodealkylation of an alkylaromatic compound, wherein a feedstock comprising greater than 50 mole % of $C_6$–$C_{12}$ single-ring, aromatics and greater than 50 mole % of $C_9$–$C_{12}$ single-ring aromatics are hydrodealkylated in the presence of a catalyst containing a zeolite MCM-22 having a silica/alumina ratio of greater than 10 and a noble metal or nickle under the reaction conditions of 600°–1000° F. (315°–540° C.), 50–500 psig, a liquid hourly space velocity of 0.5–10 $h^{-1}$ and a hydrogen circulation rate of 50–5000 scf/bbl. to produce BTX. For example, by contacting a feedstock containing 96.8 mole % of $C_9^+$ aromatics with a catalyst consisting of 65% by weight of zeolite MCM-22, 35% by weight of $Al_2O_3$ and 0.66% by weight of Pt under the conditions of 600°–900° F. (315°–480 ° C.), 200 psig, a liquid hourly space velocity of 2.5 $h^{-1}$ and a hydrogen circulation rate of 2000 scf/bbl., the content of benzene, toluene and xylene in the products obtained are 16.0–45.8 mole %, 2.7–15.4 mole % and 7.8–24.1 mole %, respectively, with the selectivity to BTX being 63.8–80.9 mole %.

U.S. Pat. No. 5,043,513, which is a continuation-in-part of U.S. Pat. No. 5,001,296, discloses a process for the catalytic hydrodealkylation of the same hydrocarbon feedstock containing alkylaromatic compounds to produce BTX.

On the basis of the prior art, an object of the present invention is to provide a new type of catalyst having higher activity and stability for the conversion of heavy aromatics containing more than nine (including nine) carbon atoms to light aromatics to produce BTX; Another object of the present invention is to provide a method for preparing said catalyst; A still further object of the present invention is to provide a process for the same conversion therewith.

SUMMARY OF THE INVENTION

The catalyst provided in this invention consists of 30–70% by weight of zeolite ZSM-5 and 30–70% by weight of γ- or η-$Al_2O_3$ as carrier, 0.1–0.5% by weight of Re, 0.1–0.5% by weight of Sn and 0.05–0.3% by weight of Pt or 0.2–0.8% by weight of Pd supported on the carrier, based on the weight of the carrier. The catalyst is prepared by mixing a Na-ZSM-5 zeolite with $Al_2O_3$ or its precursor in a predetermined amount, adding a solution of nitric acid, followed by mixing and kneading, then extruding and finally calcinating to give a carrier; ion exchanging said carrier with a solution of ammonium salt to enable the exchanged sodium cation content in the zeolite ZSM-5 to be above 90%; and impregnating said carrier with a solution of the mixture of the precursors of metal components of Re, Sn and Pt or Pd, and then calcinating to give a catalyst. Contacting the $C_9^+$ heavy aromatics with the catalyst of the present invention under the reaction conditions of a reaction temperature of 350°–450° C., a reaction pressure of 0.5–3.5 MPa, a weight hourly space velocity of 1–5 $h^{-1}$ and a hydrogen/hydrocarbon ratio (v/v) of 500–1200 to give benzene, toluene and xylene.

DETAILED DESCRIPTION OF THE INVENTION

The catalyst provided in the present invention consists of zeolite ZSM-5 and γ- or η-$Al_2O_3$, preferably zeolite ZSM-5 and γ-$Al_2O_3$ as carrier, and Re, Sn and Pt or Pd supported on the carrier. On the basis of the weight of the carrier, the zeolite ZSM-5 in the carrier comprises 30–70% by weight; preferably 40–60% by weight; $Al_2O_3$ comprises 30–70% by weight, preferably 40–60% by weight; and the supported metals are 0.1–0.5% by weight of Re, 0.1–0.5% by weight of Sn and 0.05–0.3% by weight of Pt or 0.2–0.8% by weight of Pd.

The process for preparing the catalyst provided in this invention comprises mixing a Na-ZSM-5 zeolite with $Al_2O_3$ or its precursor in a predetermined amount, adding a solution of nitric acid followed by mixing and kneading, then extruding and finally calcinating to give a carrier; ion exchanging said carrier with a solution of ammonium salt to enable the exchanged sodium cation content in the zeolite ZSM-5 to be above 90%; and impregnating said carrier with a solution of the mixture of the precursors of metal components of Re, Sn and Pt or Pd, and then calcinating to give a catalyst.

Specifically, the above-mentioned process comprises the following steps:

1. Preparing the carrier: mixing a Na-ZSM-5 zeolite with $Al_2O_3$ or its precursor in a predetermined amount, then adding a solution of nitric acid with a concentration of 1–5% by weight, preferably 1.5–3.0% by weight, in an amount of 25–60%, preferably 35–45% of the weight of the mixed powder material, mixing and kneading, then extruding and drying, and finally calcinating at 450°–650° C., preferably 500°–600° C. in air for 2–8 hours, preferably 3–6 hours;

2. Ion exchanging with ammonium cations: ion exchanging the carrier prepared above with a 0.1–0.8N, preferably 0.2–0.6N solution of ammonium salts selected from $NH_4Cl$ and $NH_4NO_3$ at a temperature between room temperature and 120° C., preferably 85°–100° C. for 1–6 hours, preferably 1–3 hours each time, until the exchanged sodium cation content in the Na-ZSM-5 zeolite reaches above 90%, then filtering and washing, and finally drying;

3. Introducing metal components: impregnating the ammonium cations exchanged carrier with a solution of the mixture of the precursors of said metal components under the conditions of room temperature and a liquid/solid ratio of 1–3 for 8–60 hours, preferably 12–36 hours, then filtering and drying, and finally calcinating at 400°–600° C., preferably 450°–550° C. in air for 1–10 hours, preferably 3–6 hours.

The metal Sn component can also be introduced into the catalyst by pre-impregnating in $Al_2O_3$ or its precursor.

The zeolite ZSM-5 used in the catalyst according to the present invention can be prepared by any well-known techniques including the method in the presence or absence of amine. The prefered zeolite ZSM-5 has a silica to alumina ratio of 15–150, and a crystal size of less than 1 µm. The precursors of $Al_2O_3$ can be selected from all kinds of hydrated aluminas, including amorphous aluminium hydroxide; and $Al_2O_3$ is prepared by heating a hydrated alumina obtained by various known techniques, such as by precipitation of sodium meta-aluminate and aluminum sulfate, by precipitation of sodium meta-aluminate and carbon dioxide, by hydrolysis of alkyl aluminum or by hydrolysis of alkoxyl aluminum. Preferably, $Al_2O_3$ is $\gamma$-$Al_2O_3$ which is produced by hydrolysis of alkoxyaluminium, preferably by hydrolysis of alkoxyaluminium with less carbon atoms as disclosed in CN 85100218. The precursors of metal components used in the present invention are those commonly used in the techniques for preparing catalysts, such as chloroplatinic acid, palladium chloride, perrhenic acid or tin chloride.

The catalyst provided in this invention can be applied in the process for the conversion of heavy aromatics to light aromatics to produce BTX, which comprises contacting the $C_9^+$ heavy aromatics with said catalyst under the conditions of a reaction temperature of 350°–450° C., a reaction pressure of 0.5–3.5 MPa, a weight hourly space velocity of 1–5 $h^{-1}$ and a hydrogen/hydrocarbon ratio (v/v) of 500–1200, then fractionating the product.

The catalyst provided in the present invention possesses higher activity for converting heavy aromatics and higher yield of BTX than those of the prior art. For example, the catalyst provided in the present invention achieves 2–6 times activity and yield of BTX as high as those provided in the prior art in the conversion of heavy aromatics containing 97.95% by weight of $C_9^+$ aromatics under the same reaction conditions.

The catalyst provided in the present invention is characterized by good stability and small hydrogen consumption, for example, the coke on the catalyst after reaction for 1000 hours in the heavy aromatics containing 97.95% by weight of $C_9^+$ aromatics was only 6.1% by weight, and the hydrogen consumption was only 2.3% by weight.

In the process for preparing the catalyst provided in the present invention, the zeolite was extruded before ion exchange, thus leading to a reduction of the loss of the zeolite during the ion exchange, a reduction of the environmental pollution by dust, a great decrease of the time required for filtration and wash, and an increase of the recovery of the zeolite, especially for the large scale production, compared with the technique conventionally used in the art, which comprises ion exchanging before extruding.

Heavy aromatics can be recovered to BTX on the catalyst provided in the present invention at lower reaction temperature than the catalysts of the prior art, and the operation parameters can vary in wider range.

The following examples are used to further illustrate the present invention, but they are not intended to limit the scope of the present invention.

EXAMPLES 1–4

Preparation of the Catalysts Provided in the Present Invention

A predetermined amount of zeolite ZSM-5 (Industrial product, with the crystal size of less than 1 µm) was mixed with a predetermined amount of $Al_2O_3$ ($\gamma$-$Al_2O_3$ was prepared as described in CN 85100218, while $\eta$-$Al_2O_3$ was an industrial product), then added 2% solution of nitric acid in an amount of 40% of the weight of the powder material. The mixture was mixed and kneaded, then extruded, dried at 110°–120° C., and calcinated at 550° C. in air for 4 hours to give a carrier.

10 g of the carrier obtained above was exchanged with 20 ml of 0.5N $NH_4Cl$ solution at 90°±10° C. for 2 hours. The mixture was filtered, washed and dried at 110°–120° C.

The above ammonium cations exchanged carrier was impregnated with a predetermined amount of solution of the mixture of the precursors of metal components under the conditions of room temperature and a liquid/solid ratio of 2 for 24 hours. The mixture was filtered, dried at 110°–120° C., calcinated at 500° C. in air for 4 hours, thus obtained the catalyst samples, designated as catalysts A, B, C and D, respectively.

Chloroplatinic acid and perrhenic acid which were used as the precursors of metal components were each commercially available products, and the concentrations of them when used in Examples were 2.86 mg/ml and 11.8 mg/ml, respectively. Palladium chloride was a product of chemical pure grade, and was used in a 1% by weight solution formed by dissolving in a suitable amount of hydrochloric acid solution. Tin chloride was a product of chemical pure grade, and was also used in a 1% by weight solution formed by dissolving in a suitable amount of water.

Some parameters related to the above-mentioned catalyst samples were listed in Table 1, in which the amounts of the zeolite ZSM-5 and $Al_2O_3$ as well as the active metal components were represented by weight percentage based on the weight of the carrier.

In order to demonstrate the characteristics of the catalyst provided in the present invention, a catalyst sample comprising Pt was prepared as comparative catalyst from the zeolite ZSM-5 with a silica/alumina ratio of 500 according to the teachings described in U.S. Pat. No. 4,341,622. The related parameters were listed in Table 1.

TABLE 1

| Example | 1 | 2 | 3 | 4 | Comparative Catalyst |
|---|---|---|---|---|---|
| Zeolite ZSM-5 | | | | | |
| $SiO_2/Al_2O_3$ | 60 | 60 | 60 | 60 | 500 |
| Amount, wt % | 40 | 60 | 60 | 60 | 60 |
| $Al_2O_3$ | | | | | |
| Crystal Form | γ | γ | γ | η | γ |
| Amount, wt % | 60 | 40 | 40 | 40 | 40 |
| Metal Cont. wt % | | | | | |
| Pt | 0.05 | 0.05 | 0.10 | 0.0 | 0.10 |
| Pd | 0.0 | 0.0 | 0.0 | 0.5 | 0.0 |
| Re | 0.10 | 0.10 | 0.15 | 0.10 | 0.0 |
| Sn | 0.12 | 0.12 | 0.12 | 0.12 | 0.0 |
| Catalyst Number | A | B | C | D | Comparative Catalyst |

EXAMPLES 5–7

Preparation of the Catalysts Provided in the Present Invention

γ-$Al_2O_3$ powder comprising 40% by weight of the carrier was impregnated with a predetermined amount of $SnCl_2$ solution under the conditions of room temperature and a liquid/solid ratio of 2 for 15 hours. The impregnating solution was evaporated to dryness at 110°–120° C., then added zeolite ZSM-5 comprising 60% by weight of the carrier. The mixture was mixed homogeneously. Then the mixture was made into a gel with $HNO_3$ solution and extruded as described in Examples 1–4, thus obtained the carrier. The carrier was exchanged with ammonium cations, then impregnated with a predetermined amount of chloroplatinic acid and perrehenic acid, and further processed as in Examples 1–4, thus obtained the catalyst samples E, F and G.

The related parameters of the above-mentioned catalyst samples were listed in Table 2.

TABLE 2

| Example | 5 | 6 | 7 |
|---|---|---|---|
| $SiO_2/Al_2O_3$ of Zeolite ZSM-5 | 60 | 120 | 25 |
| Sn Cont. in $Al_2O_3$, wt % | 0.12 | 0.35 | 0.12 |
| Metal Cont., wt % | | | |
| Pt | 0.05 | 0.20 | 0.05 |
| Re | 0.10 | 0.40 | 0.10 |
| Catalyst Number | E | F | G |

EXAMPLE 8

The catalyst provided in the present invention can be applied in the conversion of $C_9^+$ heavy aromatics to light aromatics under some technological conditions.

The catalysts provided in the present invention and the comparative catalyst were evaluated under the conditions of a reaction temperature of 400° C., a reaction pressure of 1.0 MPa, a weight hourly space velocity of 2.0 $h^{-1}$ and a hydrogen/hydrocarbon ratio (v/v) of 1000 by using the heavy aromatic byproducts (containing 97.95% by weight of $C_9^+$ aromatics) from the reformating, disproportionating and isomerizing process in a plant as the feedstock. The evaluation was performed in a 10 ml reaction equipment.

The amount of the catalyst charged was 5 g, and hydrogen was passed once. The results obtained was listed in Table 3.

Under different process conditions, the catalysts provided in the present invention were evaluated with the results listed in Table 4.

In Table 3 and 4,

Conversion of $C_9^+$ aromatic, % by weight=(the content of $C_9^+$ aromatic in the feedstock–the content of $C_9^+$ aromatic in the product)/(the content of $C_9^+$ aromatic in the feedstock) ×100%

The feedstock used consists of (% by weight): $C_8^-$ alkanes and cycloalkanes, 0.47; $C_8$ aromatics, 1.58; $C_9$ aromatics, 21.42; $C_{10}$ aromatics, 44.73; $C_{11}$ aromatics, 13.80; and $C_{12}^+$ aromatics, 18.00.

It can be seen from the data in Table 3 and in Table 4 that the catalysts provided in the present invention can be applied in the conversion of heavy aromatics to light aromatics under certain process conditions, and achieve higher conversion of $C_9^+$ aromatics and higher yield of BTX than those of the prior art.

TABLE 3

| Catalyst | A | C | G | Comparative Catalyst |
|---|---|---|---|---|
| Distribution Prod., wt % | | | | |
| $C_8^{N+P}$ | 3.0 | 2.2 | 2.4 | 1.0 |
| B | 3.7 | 4.0 | 6.8 | 2.0 |
| T | 7.0 | 8.2 | 23.5 | 4.1 |
| X | 12.2 | 13.0 | 32.4 | 6.3 |
| $C_9^+$ Arom. Conv., wt % | 24.3 | 25.7 | 64.3 | 11.4 |
| BTX yield, wt % | 22.9 | 25.2 | 62.7 | 10.8 |

TABLE 4

| Catalyst | B | B | D | E | F |
|---|---|---|---|---|---|
| Process conditions | | | | | |
| Reac. Temp., °C. | 390 | 390 | 390 | 390 | 430 |
| Reac. Pres., MPa | 1.0 | 1.0 | 1.0 | 1.5 | 3.0 |
| WHSV, $h^{-1}$ | 2 | 4 | 2 | 2 | 2 |
| $H_2$/HC(v/v) | 1000 | 1000 | 1000 | 1000 | 600 |
| Distribution Prod., wt % | | | | | |
| $C_8^{N+P}$ | 2.3 | 2.0 | 3.1 | 3.0 | 5.1 |
| B | 4.3 | 4.1 | 4.4 | 4.4 | 6.5 |
| T | 8.4 | 8.2 | 8.5 | 8.6 | 16.3 |
| X | 13.8 | 13.0 | 14.1 | 14.2 | 17.0 |
| $C_9^+$ Arom. Conv., wt % | 27.2 | 25.6 | 28.5 | 28.6 | 43.6 |
| BTX yield, wt % | 26.5 | 25.3 | 27.0 | 27.2 | 39.8 |

EXAMPLE 9

The catalysts provided in the present invention possess higher stability and lower hydrogen consumption.

Catalyst E was tested for its stability by using $C_9^+$ heavy aromatics of the same composition as those mentioned above under the conditions of 390°–400° C., 1.0–1.3 MPa, a weight hourly space velocity of 2 $h^{-1}$ and a hydrogen/hydrocarbon ratio (v/v) of 1000 in a 50 ml middle-type reaction equipment, the amount of the catalyst charged was 20 g. The product had the following composition (% by weight): $C_8^-$ alkanes and cycloalkanes, 3.4; benzene, 4.7; toluene, 8.2; ethylbenzene, 0.1; p-xylene, 2.9; m-xylene, 6.6; o-xylene, 2.7. The conversion of $C_9^+$ aromatic was 27.0% by weight; the yield of BTX was 25.2% by weight. After continueously running for 1000 hours, the coke on the catalyst was only 6.1% by weight, and the hydrogen consumption was only 2.3% by weight.

What is claimed is:

1. A catalyst comprising from 30 to 70 wt % of zeolite ZSM-5 and from 70 to 30 wt % of γ- or η-$Al_2O_3$ as a carrier, and from 0.1 to 0.5 wt % of Re, from 0.1 to 0.5 wt % of Sn and from 0.05 to 0.3 wt % of Pt or from 0.2 to 0.8 wt % of Pd based on the weight of the carrier supported on the carrier.

2. The catalyst of claim 1, wherein the carrier comprises from 40 to 60 wt % of zeolite ZSM-5 and from 60 to 40 wt % of γ- or η-$Al_2O_3$.

3. The catalyst of claim 1, wherein the carrier comprises zeolite ZSM-5 and γ-$Al_2O_3$.

4. A method for preparing the catalyst of claim 1, comprising the steps of:
   (a) mixing a Na-ZSM-5 zeolite with $Al_2O_3$ or its precursor;
   (b) adding a solution of nitric acid to the mixture, followed by mixing, kneading, extruding and calcining to provide a carrier;
   (c) performing an ion exchange of the carrier with a solution of ammonium salt such that an exchanged sodium cation content in the ZSM-5 zeolite is above 90%; and
   (d) impregnating the carrier with a solution of a mixture of precursors of the Re, Sn and Pt or Pd, followed by calcination.

5. The method of claim 4, wherein the ZSM-5 zeolite has a silica to alumina molar ratio of 15 to 150, and a crystal size of less than 1 μm.

6. The method of claim 4, wherein the Na-ZSM-5 zeolite is mixed with $Al_2O_3$, and wherein the $Al_2O_3$ is produced by heating a hydrated alumina.

7. The method of claim 6, wherein the hydrated alumina is produced by precipitation of sodium meta-aluminate and aluminum sulfate, by precipitation of sodium meta-aluminate and carbon dioxide, by hydrolysis of alkyl aluminum or by hydrolysis of alkoxyl aluminum.

8. The method of claim 4, wherein the Na-ZSM-5 zeolite is mixed with $Al_2O_3$, and wherein the $Al_2O_3$ is γ-$Al_2O_3$ obtained by hydrolysis of alkoxyaluminum followed by calcination.

9. The method of claim 4, wherein the Sn is pre-impregnated in the $Al_2O_3$ or its precursor.

10. A method for preparing benzene, toluene and xylene from $C_9^+$ heavy aromatics with the catalyst of claim 1, by contacting the $C_9^+$ heavy aromatics with the catalyst at a reaction temperature of 350° to 450° C., a pressure of from 0.5 to 3.5 MPa, a weight hourly space velocity of from 1 to 5 $h^{-1}$ and a hydrogen/hydrocarbon ratio (v/v) of from 500 to 1200.

11. A catalyst consisting of from 30 to 70 wt % of zeolite ZSM-5 and from 70 to 30 wt % of γ- or η-$Al_2O_3$ as a carrier, and from 0.1 to 0.5 wt % of Re, from 0.1 to 0.5 wt % of Sn and from 0.05 to 0.3 wt % of Pt or from 0.2 to 0.8 wt % of Pd based on the weight of the carrier supported on the carrier.

12. A catalyst effective for converting $C_9^+$ heavy aromatics to benzene, toluene and xylene, comprising from 30 to 70 wt % of zeolite ZSM-5 and from 70 to 30 wt % of γ- or η-$Al_2O_3$ as a carrier, and from 0.1 to 0.5 wt % of Re, from 0.1 to 0.5 wt % of Sn and from 0.05 to 0.3 wt % of Pt or from 0.2 to 0.8 wt % of Pd based on the weight of the carrier supported on the carrier.

* * * * *